US012741103B2

(12) United States Patent
Vaughan et al.

(10) Patent No.: US 12,741,103 B2
(45) Date of Patent: Sep. 22, 2026

(54) TYMPANIC MEMBRANE THERAPEUTIC DEVICE

(71) Applicant: AVENTAMED DESIGNATED ACTIVITY COMPANY, Bishopstown (IE)

(72) Inventors: John Vaughan, Blarney (IE); Olive O'Driscoll, Kinsale (IE)

(73) Assignee: KARL STORZ SE & Co. KG, Tuttlingen (DE)

( * ) Notice: Subject to any disclaimer, the term of this patent is extended or adjusted under 35 U.S.C. 154(b) by 1174 days.

(21) Appl. No.: 17/773,574

(22) PCT Filed: Oct. 29, 2020

(86) PCT No.: PCT/EP2020/080450

§ 371 (c)(1),
(2) Date: Apr. 29, 2022

(87) PCT Pub. No.: WO2021/084033

PCT Pub. Date: May 6, 2021

(65) Prior Publication Data

US 2022/0387223 A1 Dec. 8, 2022

(30) Foreign Application Priority Data

Nov. 1, 2019 (EP) .................................... 19206775

(51) Int. Cl.
*A61M 5/42* (2006.01)
*A61F 11/20* (2022.01)
(Continued)

(52) U.S. Cl.
CPC ............. *A61M 5/425* (2013.01); *A61F 11/20* (2022.01); *A61M 25/0084* (2013.01);
(Continued)

(58) Field of Classification Search
CPC ........ A61M 1/77; A61M 1/772; A61M 1/774; A61M 1/85; A61M 1/92; A61M 5/425;
(Continued)

(56) References Cited

U.S. PATENT DOCUMENTS 1,934,046 A * 11/1933 Demarchi ............ A61M 5/425
604/176
2,743,723 A * 5/1956 Hein .................... A61M 5/425
604/115

(Continued)

FOREIGN PATENT DOCUMENTS

KR 1020190117257 A 10/2019
WO 9511634 A1 5/1995

(Continued)

OTHER PUBLICATIONS

International Search Report, International application No. PCT/EP2020/080450. Date of mailing: Feb. 2, 2021. European Patent Office, Rijswijk, NL.

(Continued)

*Primary Examiner* — Kami A Bosworth
(74) *Attorney, Agent, or Firm* — David N. Villalpando; Jason Worgull; Jacqueline Cohen

(57) ABSTRACT

A therapeutic device (1) has a stem (3) having a distal end (60) configured for insertion in a patient's ear canal with latching by suction to the tympanic membrane so that there is no relative movement despite patient head movement. A needle (63) punctures the membrane after suction is applied by negative pressure via a lumen (66). The needle tip is located within a suction cup which grips the membrane. A hand-held control device (2) is coupled to the stem and has a user-actuated controller (8) for controlling application of negative pressure (7) to the suction lumen.

16 Claims, 9 Drawing Sheets

(51) Int. Cl.
*A61M 25/00* (2006.01)
*A61B 17/30* (2006.01)

(52) U.S. Cl.
CPC .................. *A61B 2017/308* (2013.01); *A61M 2025/0089* (2013.01); *A61M 2025/0092* (2013.01)

(58) Field of Classification Search
CPC ... A61M 2210/0662; A61M 2210/0668; A61F 11/00; A61F 11/20; A61F 11/202
See application file for complete search history.

(56) References Cited

U.S. PATENT DOCUMENTS 3,122,138 A * 2/1964 Geary .................. A61M 5/204 604/116
4,299,219 A * 11/1981 Norris, Jr. ............ A61M 5/425 604/115
6,406,453 B1 6/2002 Goode et al.
6,692,455 B2 2/2004 Goode et al.
6,743,211 B1 * 6/2004 Prausnitz ......... A61B 5/150083 604/173
6,936,023 B2 8/2005 Goode et al.
7,097,661 B2 8/2006 Perry
8,197,433 B2 6/2012 Cohen
8,332,999 B2 12/2012 Karling et al.
8,480,610 B1 7/2013 Hill
8,480,611 B1 7/2013 Alshemari
8,529,495 B1 9/2013 Alshemari
D707,822 S 6/2014 Clopp et al.
8,795,290 B2 8/2014 Konstorum et al.
8,864,774 B2 10/2014 Liu et al.
8,945,142 B2 2/2015 Schaeffer et al.
9,011,363 B2 4/2015 Clopp et al.
9,023,059 B2 5/2015 Oushin et al.
9,345,473 B2 5/2016 Fisher
9,370,448 B2 6/2016 Loushin et al.
9,504,490 B2 11/2016 Konstorum et al.
9,707,131 B2 7/2017 Shahoian
9,770,366 B2 9/2017 Liu et al.
9,782,298 B2 10/2017 Loushin et al.
10,130,515 B2 11/2018 Kaplan et al.
10,258,776 B2 4/2019 Clifford et al.
10,588,782 B2 3/2020 Skovlund
10,595,848 B2 3/2020 Woodard et al.
10,610,412 B2 4/2020 Liu et al.
10,624,792 B2 4/2020 Loushin et al.
10,632,017 B2 4/2020 Girotra et al.
10,653,446 B2 5/2020 Andreas et al.
10,653,561 B2 5/2020 Andreas et al.
10,695,224 B2 6/2020 Loushin et al.
10,736,785 B2 8/2020 Clopp
10,751,219 B2 8/2020 Vaughan et al.
10,765,560 B2 9/2020 Clopp et al.
10,792,189 B2 10/2020 Leland et al.
10,835,422 B2 11/2020 Clopp et al.
10,881,506 B2 1/2021 Angelillo et al.
10,918,525 B2 2/2021 Andreas et al.
10,966,866 B2 4/2021 Van et al.
11,116,949 B2 9/2021 Lee et al.
2002/0128600 A1 * 9/2002 Nissels ................ A61M 5/425 604/151
2007/0270745 A1 * 11/2007 Nezhat ................ A61B 5/6834 604/115
2011/0152875 A1 6/2011 Gonzales
2012/0179187 A1 7/2012 Loushin et al.
2012/0203200 A1 * 8/2012 Kenney .................. A61F 11/00 604/60
2013/0023818 A1 * 1/2013 Rosenblum .......... A61B 5/0537 604/35
2014/0276906 A1 9/2014 Andreas et al.
2014/0277050 A1 * 9/2014 Andreas ................ A61F 11/202 606/185
2015/0164695 A1 6/2015 Liu et al.
2015/0246183 A1 * 9/2015 Kavokin ............ A61M 5/3286 604/176
2018/0036035 A1 2/2018 Ruijter et al.
2018/0296243 A1 10/2018 Hanson et al.
2019/0038469 A1 2/2019 Imran et al.
2019/0192349 A1 6/2019 Vaughan et al.
2019/0282749 A1 * 9/2019 Kunis ............... A61M 25/0074
2020/0022842 A1 1/2020 Labib et al.
2020/0163800 A1 5/2020 Skovlund
2020/0237559 A1 7/2020 Loushin et al.
2020/0237560 A1 7/2020 Andreas et al.
2020/0281772 A1 9/2020 Loushin et al.
2021/0052868 A1 2/2021 Goldfarb et al.
2021/0169697 A1 6/2021 Vaughan et al.
2022/0339357 A1 * 10/2022 Hao ....................... A61M 5/20

FOREIGN PATENT DOCUMENTS

WO 2013113022 A1 8/2013
WO 2014075949 A1 5/2014
WO 2015095214 A1 6/2015
WO 2016128071 A1 8/2016
WO 2019086608 A1 5/2019
WO 2019183295 A1 9/2019

OTHER PUBLICATIONS

Written Opinion of the International Searching Authority, International application No. PCT/EP2020/080450. Date of mailing: Feb. 2, 2021. European Patent Office, Munich, DE.

* cited by examiner 62
61
60

TYMPANIC MEMBRANE THERAPEUTIC DEVICE

INTRODUCTION

The invention relates to therapy involving the tympanic membrane or "ear drum" of a patient. The primary field of the invention is the intratympanic delivery of drugs to the middle ear. Other fields of the invention include, but are not limited to, deployment of a tympanostomy tube (or "grommet") or aspiration of fluid from the middle ear.

The ear is subject to a variety of conditions or diseases for which the therapeutic delivery of drug to the middle ear is desirable. An example is Meniere's disease, a chronic condition characterized by acute vertigo attacks, tinnitus, fluctuating hearing loss and a feeling of aural fullness. Another example is tinnitus, which is often described as a ringing in the ear but can also sound like roaring, clicking, hissing or buzzing. People with severe tinnitus may have trouble hearing, working and sleeping. Another example is Otitis Media, frequently giving rise to a need for antibiotics.

The ear is especially sensitive to invasive therapy involving the tympanic membrane due to it being so thin and prone to damage, especially due to a patient moving his or her head during treatment. This problem is particularly acute where the patient is a child.

An object of the invention is to achieve effective, safe and repeatable therapy, with or without delivery of a fluid or device, at or near the tympanic membrane.

SUMMARY STATEMENTS

We describe a therapeutic device as set out in the appended claims.

Also, we describe a therapeutic device comprising:

- a stem having a distal end configured for insertion in a patient's ear canal, the stem comprising:
  - a lumen for application of suction, and having at its proximal end a suction source or a coupler for connection to a suction source,
  - a needle having a tip configured for piercing a tympanic membrane, and
  - a suction cup within which the needle tip is located, said suction cup being linked with said lumen and being configured for engaging a tympanic membrane and gripping by suction the membrane.

Preferably, the device further comprises a hand-held control device for coupling to the stem and having a user-actuated controller for controlling application of negative pressure to the suction lumen. Preferably, the needle is mounted at an acute angle to a longitudinal axis of the stem.

Preferably, the stem distal tip comprises a hub supporting the suction cup and the needle. Preferably, the hub includes a conduit to receive the lumen and is surrounded by a flexible sleeve which retains the hub in place. Preferably, the flexible sleeve integrally forms the suction cup. Preferably, the flexible sleeve is of silicone (or similar flexible materials) over-moulded construction.

Preferably, the hand-held control device comprises a housing for coupling to the stem, and a handle with trigger buttons for user actuation. Preferably, the hand-held control device comprises a coupler for connection to a suction source.

Preferably, the stem comprises a lumen linked with the needle for delivery of a therapeutic fluid, said lumen having a coupler at its proximal end for connection to a fluid source, the needle being configured for piercing the tympanic membrane and for delivering a therapeutic fluid via said needle.

Preferably, the device comprises a housing which comprises a syringe pusher for mounting of a syringe with a therapeutic fluid in fluid communication with the delivery lumen.

In one example, the needle and the suction cup are movable relative to each other for piercing of the tympanic membrane and withdrawal from the tympanic membrane.

Preferably, the needle is fixed, and the suction cup is retractable relative to the needle in a manner to ensure piercing by the needle. Preferably, the suction cup is mounted on a sleeve which is retractable relative to the needle. Preferably, the sleeve includes tensioning cables which are operatively connectable to a controller.

Preferably, the needle is arranged for delivery of a tympanostomy tube across a membrane, and retraction to leave the tube in place deployed in the membrane.

DETAILED DESCRIPTION OF THE INVENTION

The invention will be more clearly understood from the following description of some embodiments thereof, given by way of example only with reference to the accompanying drawings, in which.

In various examples we describe a therapeutic delivery device which in use latches on to the tympanic membrane and punctures it for therapeutic purposes so that the tip of a stem does not move relative to the membrane despite any patient head movement. Once there is such latching an operation is performed, in one example being delivery of a drug through the membrane and in another being deployment of a tympanostomy tube.

Advantageously, a suction action ensures that a needle is optimally located and does not move during performance of the operation such as drug delivery or tympanostomy tube placement.

Device 1

Figure 1:
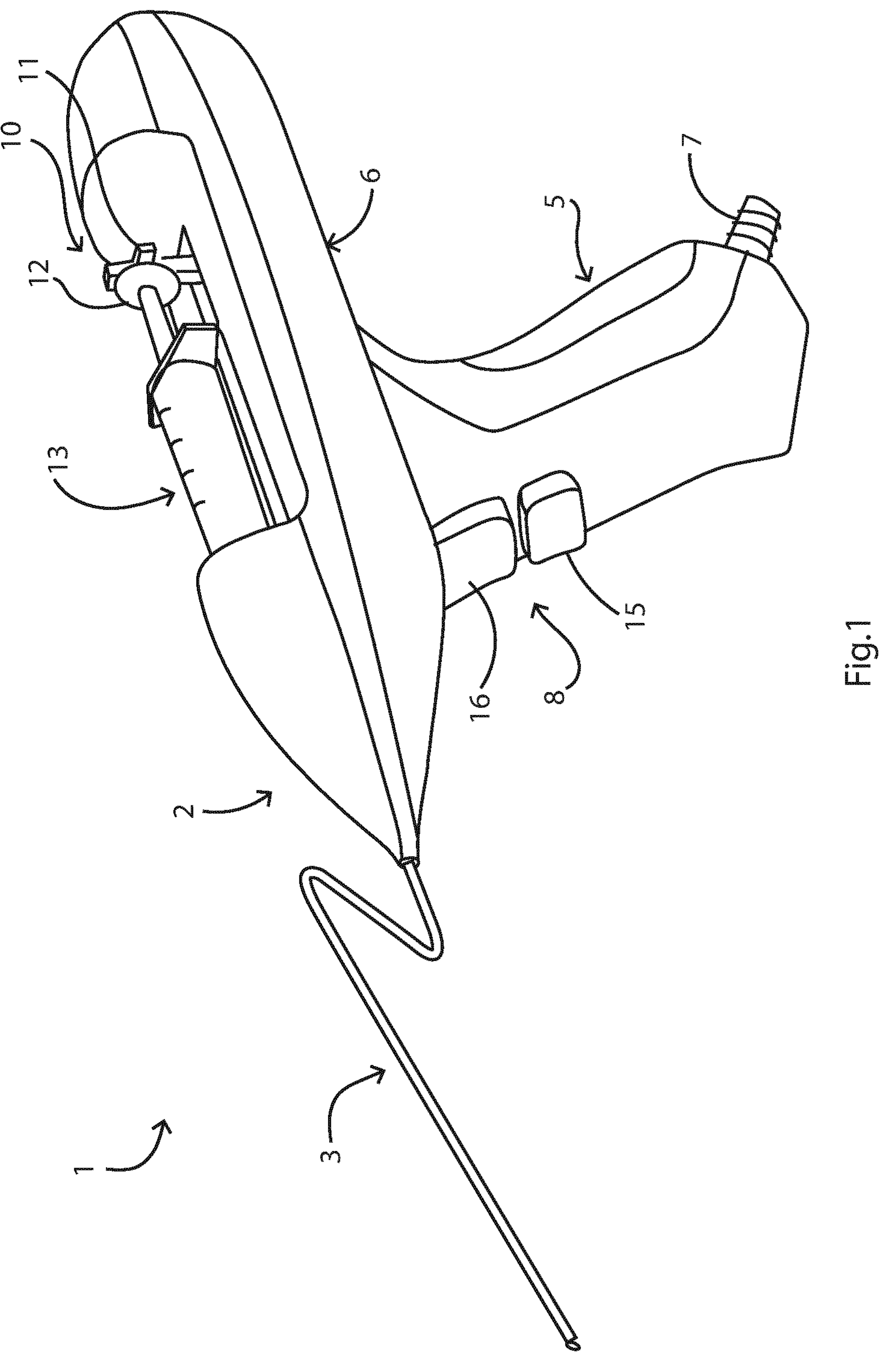
FIG. 1 is a perspective view of a therapeutic device for delivery of a pharmaceutical into the ear distal to the tympanic membrane.
Figure 2:
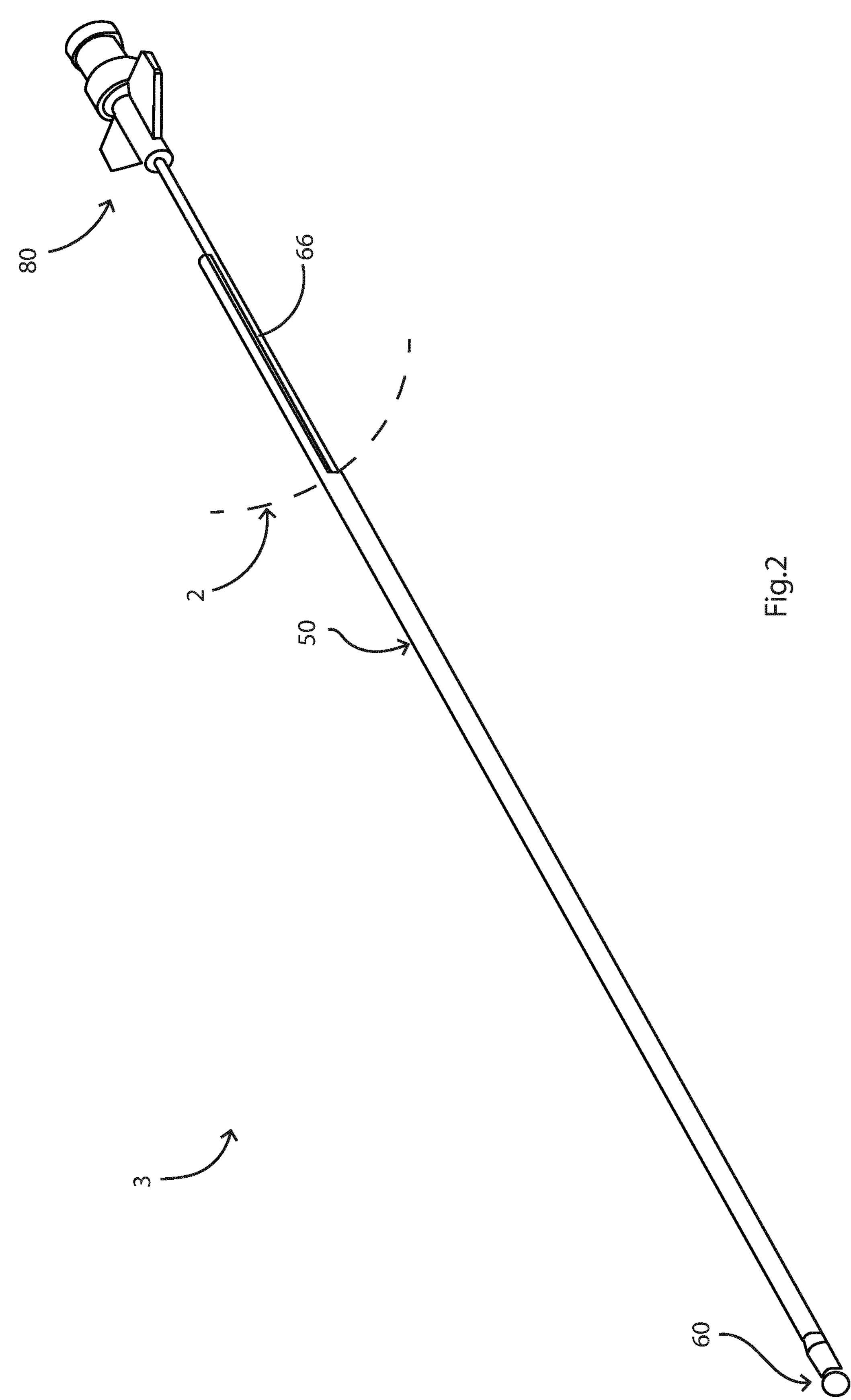
FIG. 2 is a perspective view of a stem of the device.
Figure 3:
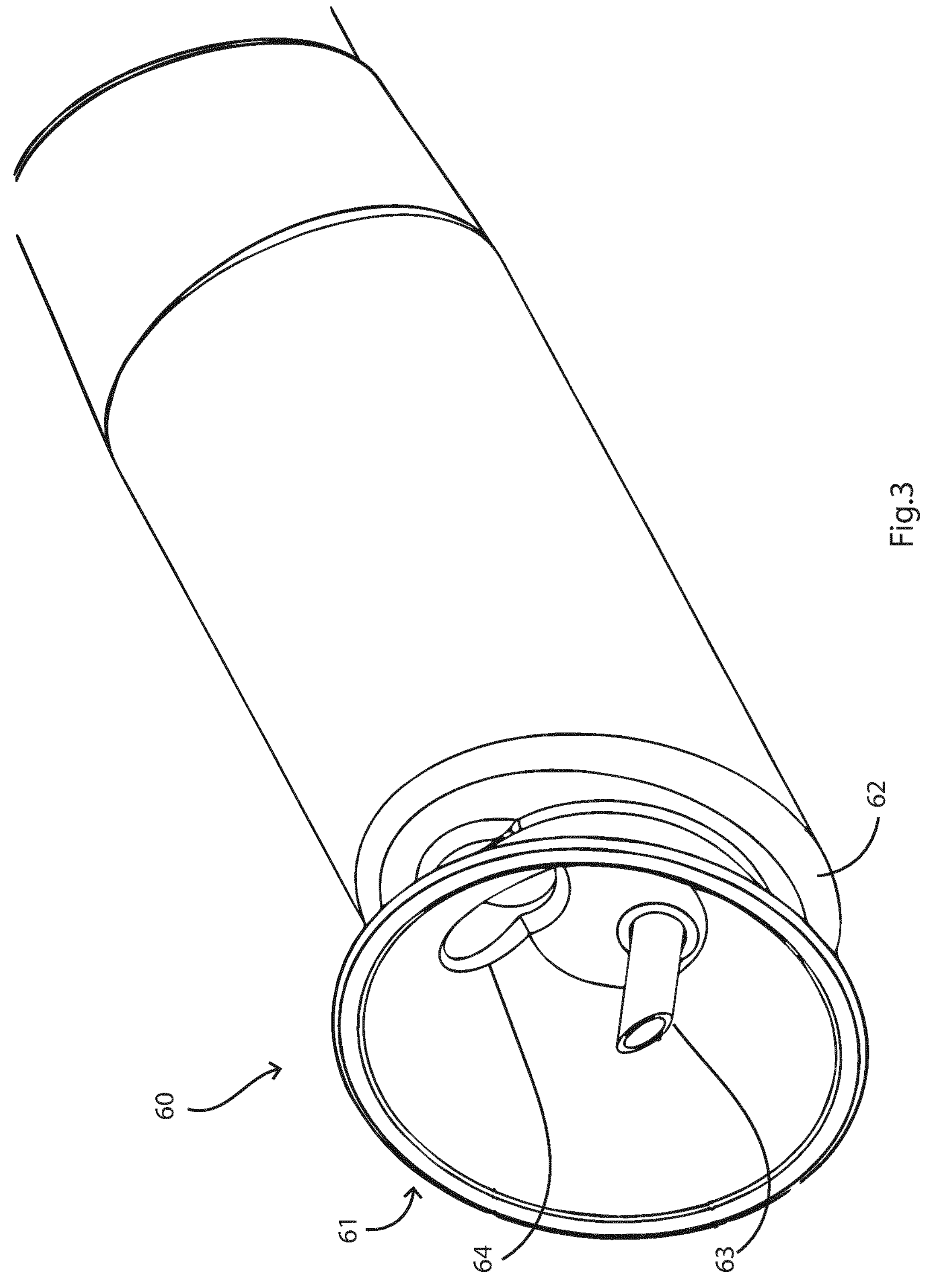
FIG. 3 is an enlarged perspective view of a distal tip of the stem.
Figure 4:
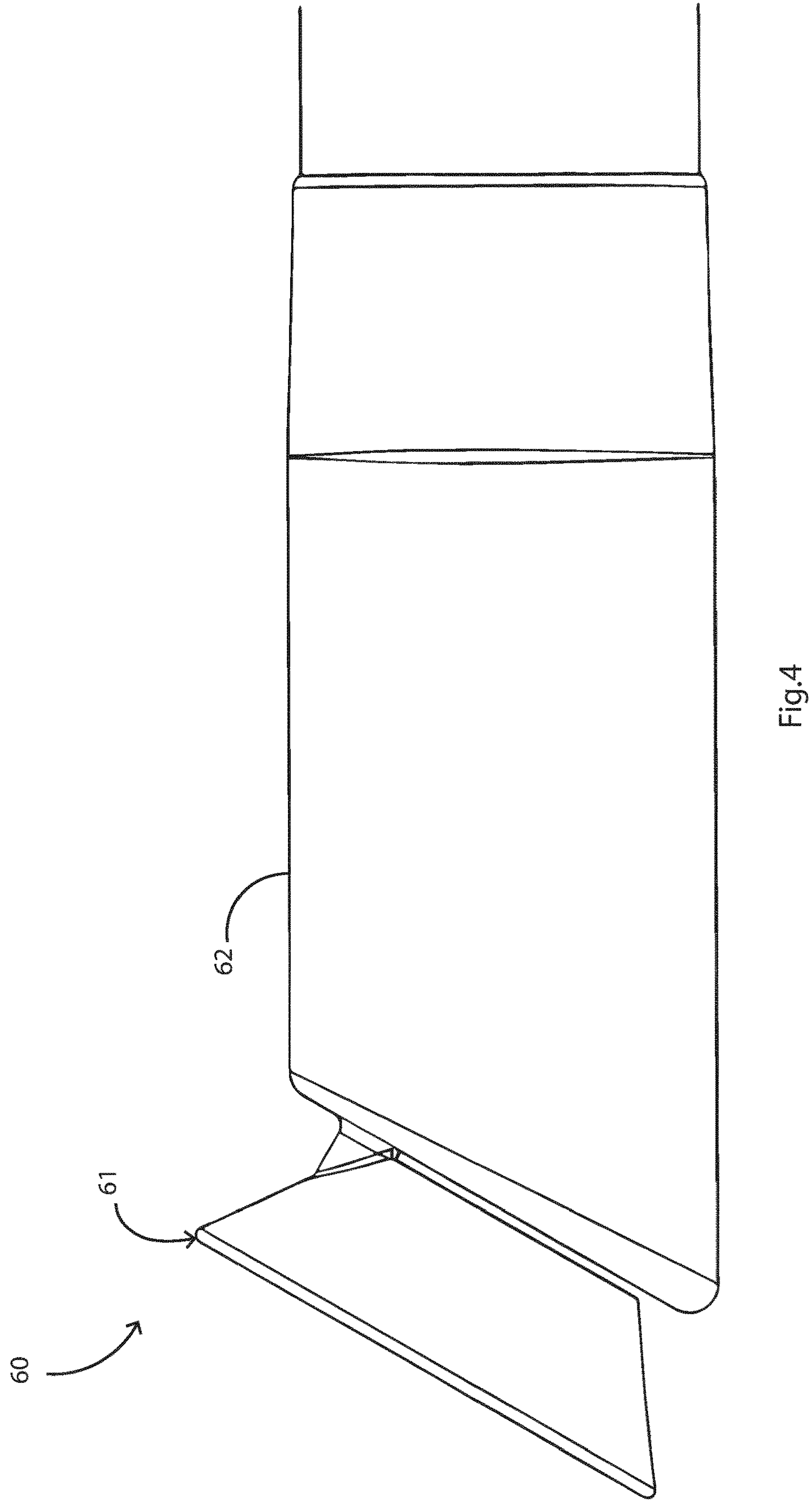
FIGS. 4 and 5 are side and side sectional views of the distal tip.

Referring to FIG. 1, a device 1 for delivery of a treatment fluid into the ear is disclosed. The device 1 comprises a hand-held housing 2 and a stem 3 of flexible construction. This stem is long and flexible such that it has a low "pushability" and will accommodate unanticipated patient movement. That is, if the stem is introduced to the ear canal and the physician pushes it forward such that the distal tip contacts the tympanic membrane (or any solid structure) the stem will collapse under the pushing force due to the flexible nature of the shaft. Furthermore, if the distal tip attaches to the patient's tympanic membrane, the stem will accommodate any unintended movement of the patient.

The housing 2 has a handle 5 and a main body 6 containing a control mechanism. The handle 5 has a coupler 7 to an external suction source and control buttons 8. Within the housing 2 there is a pressure control valve to prevent excess pressure being applied through the device 1 to the ear canal in use even if a mistake is made in the pressure delivered to the coupler 7.

The housing main body 6 comprises a syringe pusher 10 with a spring-loaded push member 11 arranged to push a piston 12 of a syringe 13.

The buttons 8 include a lower button 15 for application of suction when an external source is coupled, and an upper button 16 for drug delivery when a syringe has been inserted.

Referring to FIGS. 2 to 5 the stem 3 has a main section 50, a distal tip 60 and a proximal coupler 80 with a luer connector which connects to the housing 6 during manufacture assembly.

The tip 60 has a suction cup 61 of approximately 3 mm diameter and an angle of approximately 45° between the cup and the side walls on the distal side (stem longitudinal axis), and this angle is generally preferably in the range of 20° and 90°, and an outer lining 62 or tubular structure of the stem leading to the suction cup 61. The angle of the suction cup 61 matches the acute angle which the ear drum would sit relative to the ear canal. This angle can be particularly acute in paediatric patients.

Within the stem there is a delivery lumen 65 for delivery of a therapeutic fluid, and also a suction lumen 66. The needle 63 forms a continuation of the delivery lumen 65, being embedded at its proximal end in a plastics hub 67.

The hub 67 forms a conduit 68 which is a distal continuation of the suction lumen 66, and the conduit 68 terminates distally in a mouth 69 which is splayed out in the suction cup 61.

Figure 5:
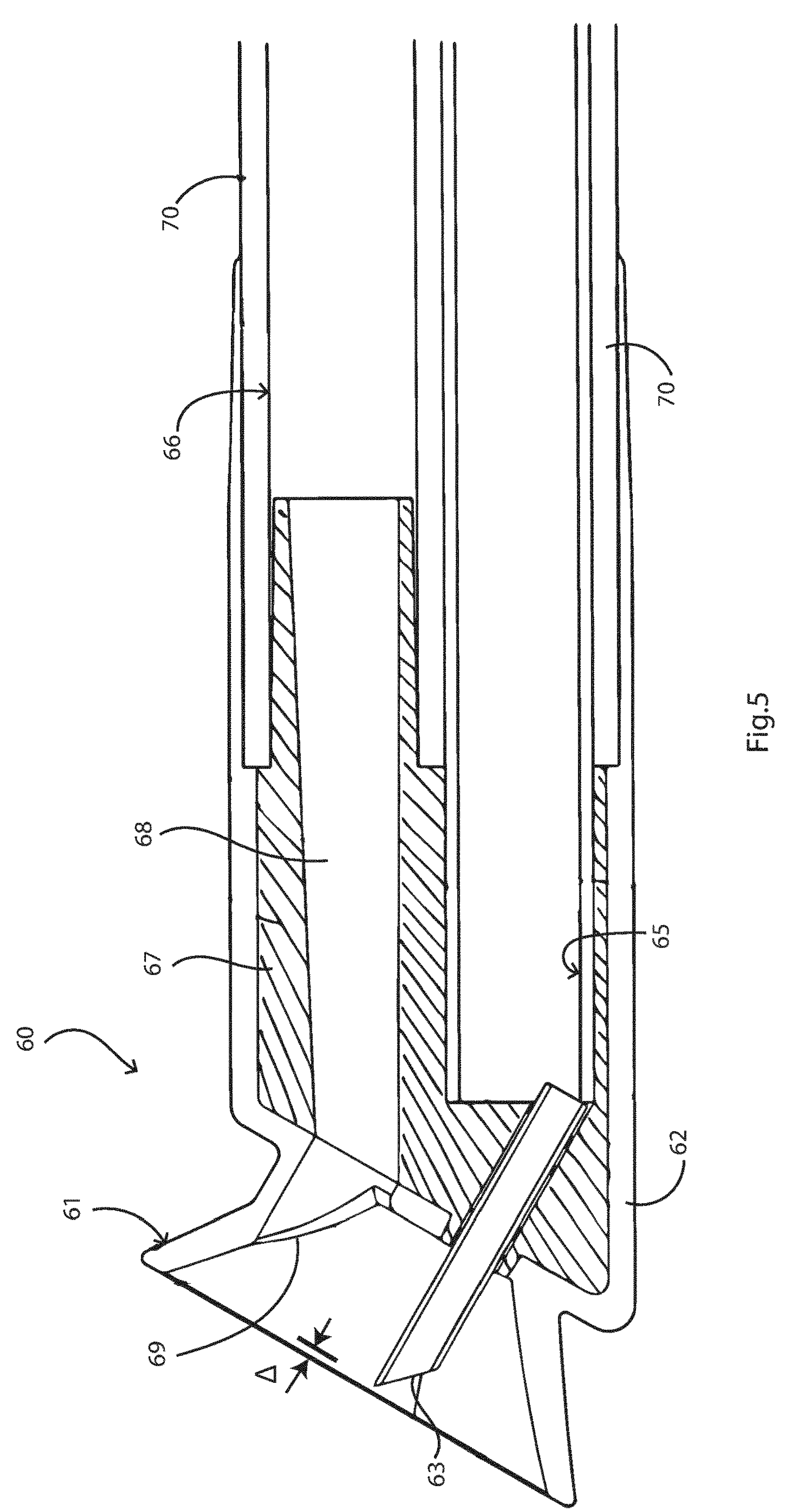

As is shown most clearly in FIG. 5, in this example, the outer lining 62 comprises a flexible silicone (medical grade) over-mould or similar material, which envelopes an outer multi-lumen liner 70 of the stem and the hub 67, and itself forms the suction cup 61 in an integral manner.

As shown in FIG. 5 there is a gap indicated by A between the end of the needle and a plane formed by a distal rim of the cup 61. Hence, the needle 63 does not protrude beyond the outer edge of the suction cup 61, ensuring that the needle cannot inadvertently puncture important structures during placement or removal of the device. As a result, the needle will only puncture when suction is applied—otherwise it is effectively sheathed within the suction cup.

The tubular liner 70 is of flexible silicone material (or in other examples a suitable medical-grade flexible material such as a thermoplastic elastomer, "TPE") to ensure that there is minimal risk of injury upon insertion of the stem distal end 60 in the ear canal. However, the silicone over-mould 62 is especially flexible, and effectively contains the hub 67, the needle 63, and the lumen 65 and 66 distal ends in a manner which ensures optimum support to these parts and flexibility in use.

Use of Device 1

The physician connects the coupler 7 to an external suction source. The syringe pusher 10 is pulled back (spring loaded and button activated) and a standard syringe is installed into the handpiece housing 6 via the standard luer connection on the handpiece, connection 80. The drug line is purged prior to use by pressing the upper button 16. The distal end 60 is placed in a patients' ear canal,—the tube 50 (double lumen) being so flexible that it cannot damage the ear drum or structures of the ear (ossicular chain) due to pushing of the flexible stem 3, this stem will collapse under this pushing force. The physician visualises the depth or location in which they are trying to deliver the drug to the tympanic membrane, preferably the anterior inferior quadrant, however they may not need to be specific as to where the distal tip 60 suctions onto the tympanic membrane due to the flexible nature of the tip 60 and short depth of penetration of the needle 63. Once the suction cup 61 is at the ear drum the surgeon pushes the lower button 15 to apply suction at the tip (very low negative pressure) to grip the tympanic membrane. The suction cup 61 latches onto the ear drum. During the latch, the needle 63 punctures the thin membrane that is the ear drum (ear drum thickness: 0.05 mm to 0.20 mm typically). This method of puncture will ensure that the needle 63 only punctures to a set depth and this depth will not be excessive that it could possibly contact important structures behind the tympanic membrane such as the ossicular chain or the middle ear wall which contains the facial nerve. The negative suction pressure is such that the device tip 60 latches and punctures the tympanic membrane, however, if the device latches to other structures such as the ear canal wall or the ossicular chain there would be insufficient suction force to penetrate these more rigid structures.

Once latched onto and the tympanic membrane is punctured the surgeon presses the upper button 16 to administer a drug. Once complete the physician releases the suction button 16 which opens the suction line to atmospheric pressure (or positive pressure) to unlatch the suction cup. The stem 3 is removed from the patient's ear canal.

Device 200

Figure 6:
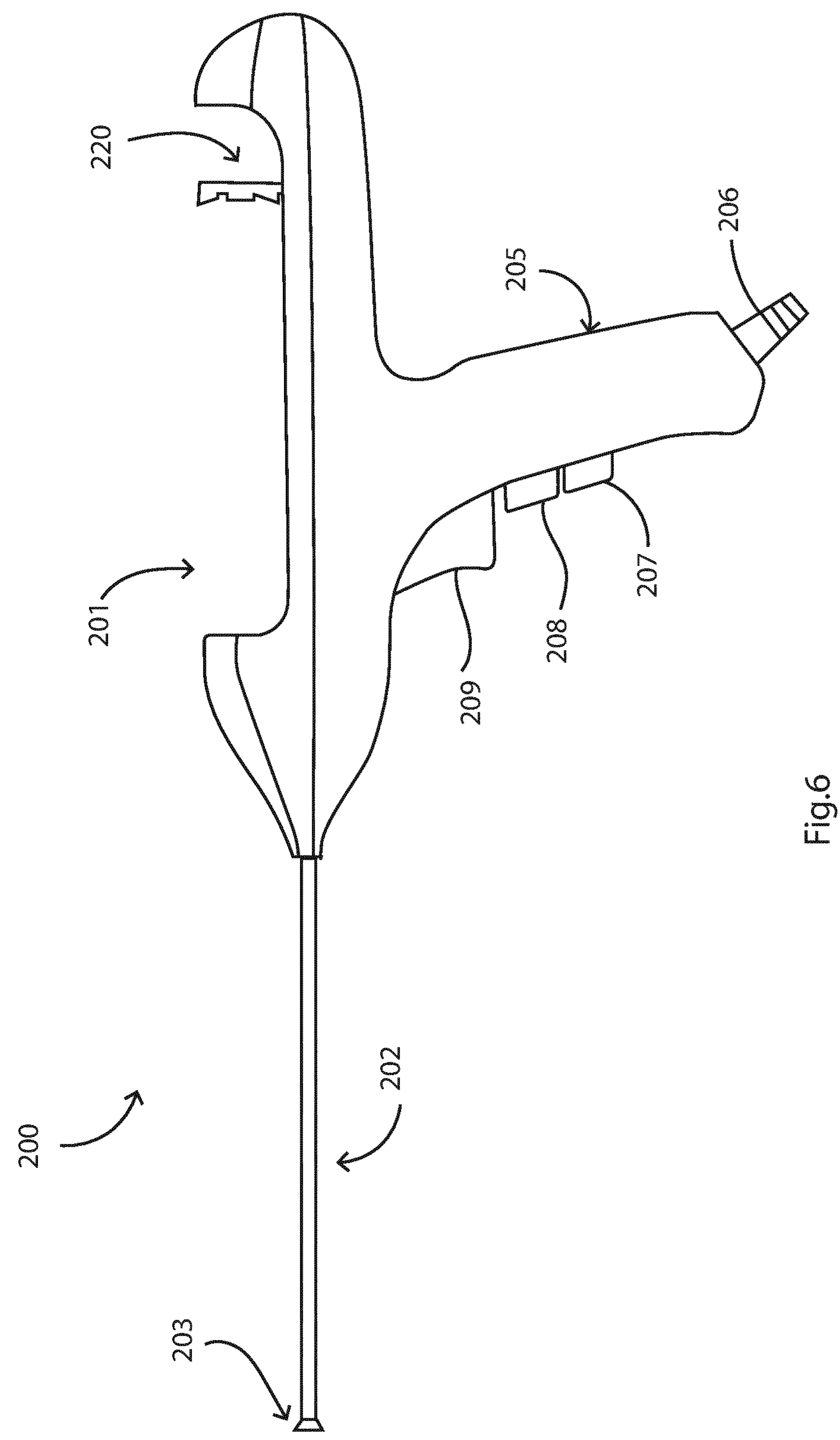
FIG. 6 is a view of an alternative device.
Figure 7:
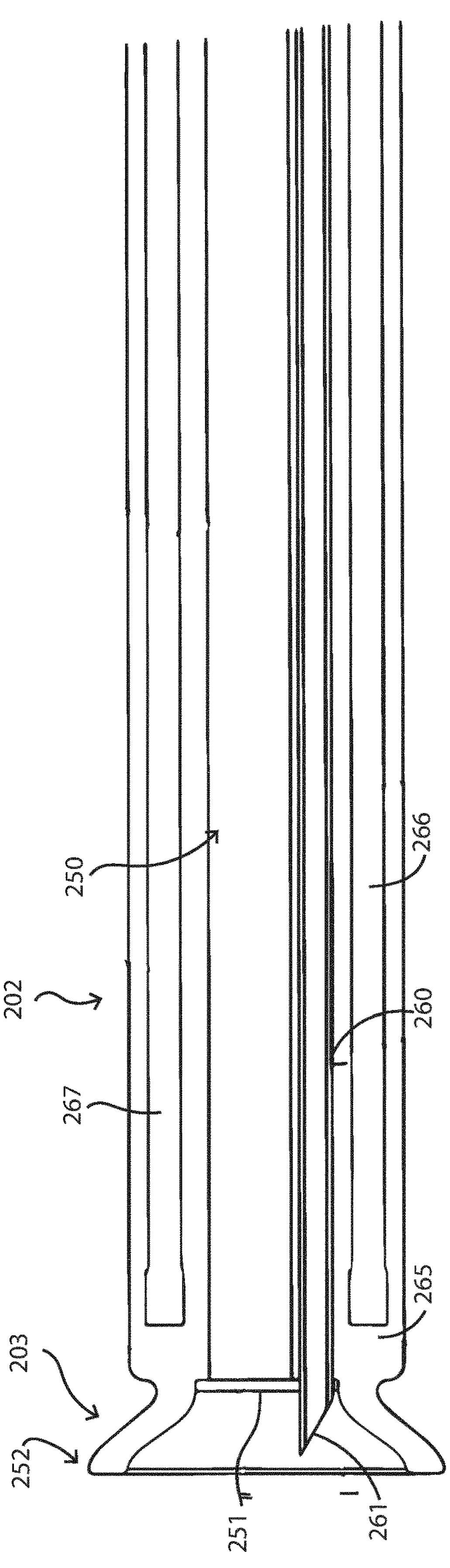
FIGS. 7 and 8 are side sectional views showing another stem distal tip in more detail.
Figure 8:
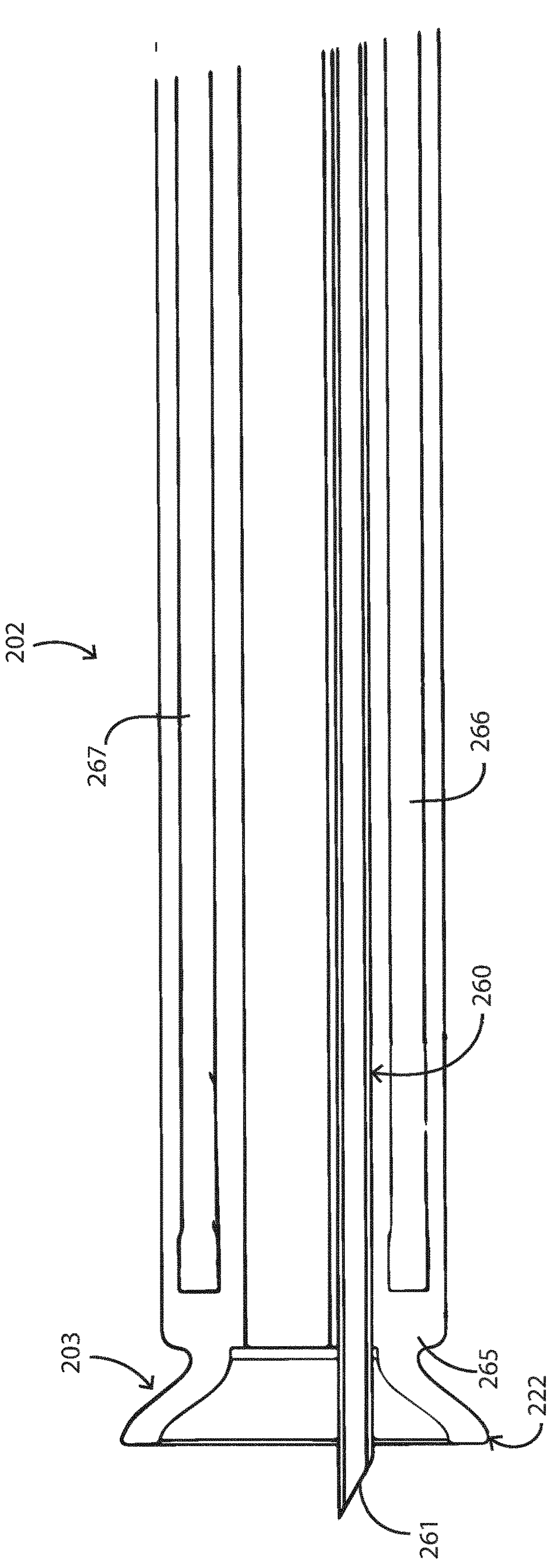

Referring to FIGS. 6 to 8 an alternative device, 200, comprises a hand-held controller 201 and a stem 202 with a distal tip 203. The controller 201 comprises a handle 205 with a coupler 220 to a suction source, a trigger button 207 for application of suction, and a trigger button 208 for drug delivery. Additionally, there is a trigger button 209 for user-activated manipulation of the tip 203, as described in more detail below. The controller 201 also comprises a syringe pusher 220, as described for the device 1.

As shown best in FIGS. 7 and 8 the stem 202 comprises a suction channel or lumen 250 terminating in a mouth 251 within a suction cup 252. A needle 260 extends parallel to the stem longitudinal axis, and continues proximally as a lumen which is more rigid than the surrounding parts of the stem, for the full length of the stem back proximally to the controller 201. The needle is fixed in position, not being movable. The needle has a tip 261 configured for piercing the tympanic membrane. In this example the length of the needle and tube which continues proximally from the needle is 300 mm, in general being long enough for the necessary rigidity for piercing but not long enough to provide too much pushing strength.

The stem 202 comprises a tubular structure 265 of flexible medical grade silicone material (or other suitable flexible material such as TPE), which terminates distally as the suction cup 252. There are a number of tensioning cables 266 and 267 extending longitudinally through the structure 265, terminating adjacent the suction cup 252.

Advantageously, there is a simultaneous action of gripping the tympanic membrane without risk of damage, while delivering a drug through the needle 63 to the distal side of the membrane. The suction action ensures that the needle is optimally located and does not move during drug delivery.

Other advantages are the user can visualise placement of the suction cup 252 to ensure correct location and the trigger 209 can be pushed once the physician is satisfied to deploy.

In this case the distal edge of the suction cup is at right angles to the longitudinal axis, however in other examples it is at an acute angle to this axis distally of the cut, as is case for the device 1.

Use of Device 200

In use the stem is inserted to the ear canal as described for the device 1, and suction is applied to grip the tympanic membrane by the user pressing the button 207. Then, with actuation of the trigger 209 the user causes withdrawal of the tubular structure 265 relative to the needle 260 (by use of the cables 266 and 267), thereby compressing the tubular structure in the direction towards the right, form the position shown in FIG. 7 to that shown in FIG. 8. Alternatively, the cables 266 and 267 maintain the length of the flexible shaft 202 and the needle 261 moves relatively to 251. This has the effect of causing the needle to relatively protrude as shown in FIG. 8. At this stage the user actuates delivery of a therapeutic fluid via the needle 260 by pushing the button 208, while the needle protrudes through the tympanic membrane as it is gripped by the suction cup 252.

Upon completion of delivery, the tension is gradually released from the cables 266 and 267, so that the needle moves proximally relative to the suction cup out of engagement with the membrane For either of the devices 1 and 200 any of a wide range of therapeutic fluids may be delivered, examples of such drugs are set out in the following table. Note: drugs delivered to the middle ear are not limited to those within this table, which are mentioned by way of example only.

| Clinical Condition | Drug Delivered |
|---|---|
| Menieres Disease | Steroids |
| | Dexamethasone |
| Acute Otitis Media | Quinolone Antibiotics |
| | Ciprofloxacin |
| | Steroids |
| | Dexamethasome |
| Tinnitus | Gacyclidine |
| Sudden hearing loss | Steroids |
| | Dexamethasone |

Alternative Devices

The devices of the invention latch onto the tympanic membrane by suction so that the location of a distal stem tip remains fixed relative to the membrane despite patient head movement that might occur. Also, the distal tip pierces the membrane. In the example devices 1 and 200 there is delivery of a therapeutic fluid through the membrane where it is pierced. However, in other examples different therapies may be performed. One example is aspiration in which there is suction of infection fluid from the middle ear, in the unusual cases where broad spectrum antibiotic is not suitable.

In another example there is deployment of a tympanostomy tube in a manner as known in the art for example as described for example in WO2014/075949 and WO2019/086608. Such a device would have the suction lumen and cup for latching onto the membrane. The stem would also include a deployment needle which, in addition to puncturing the membrane, would carry a tube with a distal flange which is opened when it is located distally of the membrane. Such a needle may perform the initial membrane puncturing in addition to tube deployment. The distal tube flange may be opened by being released by a retainer to assume a default shape, or the tube may be deformed by pulling through the needle.

If it is the former arrangement, the device may include a pre-loaded tympanostomy tube comprising a proximal flange, an inter-lumen connector, and a distal flange, and in which the proximal flange comprises passageway; and in which in a pre-deployment position device retainer fingers extend through the proximal flange passageways and press the tube distal flange inwardly. In such an arrangement, the device may have a stem connected to a deployment mechanism or having a coupler for connection to a deployment mechanism; the needle having the tip to pierce a tympanic membrane, the needle having a longitudinal axis; and the retainer has a plurality of fingers extending axially at a distance from said longitudinal axis; and the retainer is movable from a pre-deployment distal position at which it is adapted to press radially inwardly against a tube distal flange to retain said distal flange in a folded position, to a deployment proximal position at which a tube distal flange is free to spring out radially to a deployed position. Preferably there are at least two diametrically opposed retainer fingers and preferably the fingers have an arcuate cross-sectional shape with a concave internal surface.

Device 300

Figure 9:
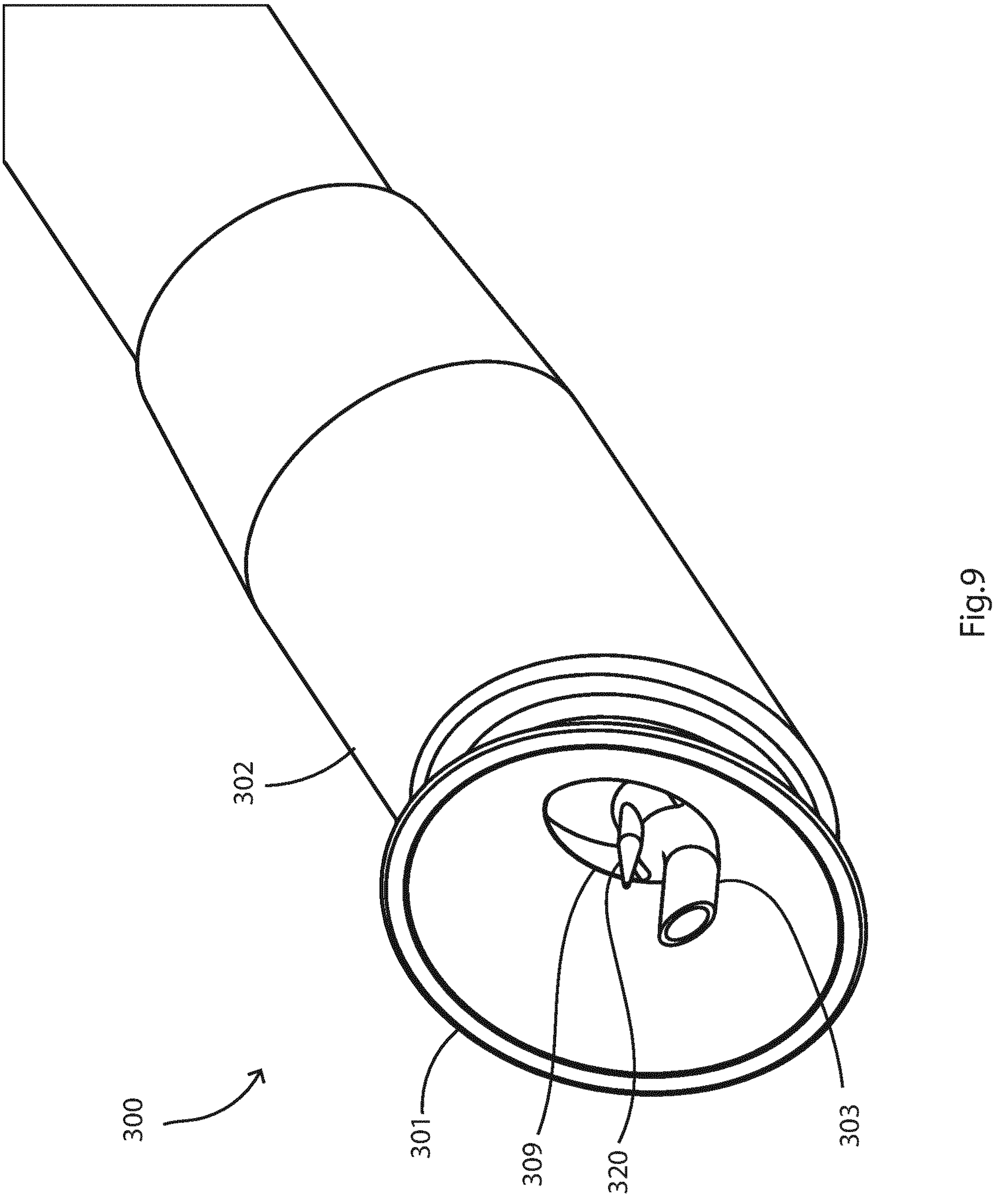
FIG. 9 is an enlarged perspective view of a distal tip of an alternative stem.

Referring to FIG. 9 in another example a stem 300 extends from a housing as described in any of the above embodiments. The stem 300 has an outer tubular structure 302 terminating at its distal end with a suction cup 301 and a needle 303 which is akin to the needle 63 and has the same purpose, being at the end of a lumen. In this case a second needle 320 is provided, and which does not have a lumen. However, it communicates with an electronic circuit within the handpiece via a wire connection within the stem wall 302. The needle 303 also has a wired connection to this electronics board. During use, when the device applies suction both needles would penetrate the site tissue. The circuit applies an electrical drive across the two needles 303 and 320, and measurements are made of a parameter such as impedance or capacitance. The circuit within the handle of the device has an interface to an output device such as an LCD screen or LED lights. The circuit is also linked with a sensor to measure the pressure within the suction line to the cup 301. Through these two inputs, the circuit generates an output to inform the user whether drug could be administered to the correct location. That is, if pressure within the suction line increases i.e. the device suctions or attaches onto a target site the device would then measure the capacitance/impedance across the two needles. If that measurement is greater than a threshold value then the circuit could distinguish whether the user has attached to the tympanic membrane or to the ear canal wall. The circuit would display a go-no-go decision to the user on whether to administer drug by pressing the trigger button or to unlatch from suctioning and reposition the device.

In an alternative embodiment the two electrodes required to measure capacitance or impedance are within a single needle linked by cables such as a coaxial insulated cable to the circuit.

A major advantage of this embodiment is that the physician could use this with no visualisation aids, such as operating microscope/otoscope, and could ensure accurate delivery of the drug to the correct location.

The invention is not limited to the embodiments described but may be varied in construction and detail. For example, in another example the sleeve does not retract, but the needle protrudes to achieve the relative longitudinal motion. Also, as noted above where a part is resilient and flexible it may be of any suitable medical-grade material such as TPE.

The invention claimed is:

1. A therapeutic device comprising:

an ear canal stem having a distal end for insertion in a patient's ear canal, the stem comprising:

a lumen for application of suction, the lumen having at its proximal end a suction source or a coupler for connection to a suction source, a needle having a tip for piercing a tympanic membrane, and a suction cup, positioned at the distal end of the stem, within which the tip of the needle is located, the suction cup being linked with the lumen that is for application of suction and being configured for engaging the tympanic membrane and gripping the membrane by suction, wherein the stem further comprises a lumen linked with the needle for delivery of a therapeutic fluid, the lumen that is linked with the needle for delivery of the therapeutic fluid having a proximal end with a coupler for connection to a fluid source, the needle being configured for piercing the tympanic membrane and for delivering the therapeutic fluid.

2. The therapeutic device of claim 1, further comprising a hand-held control device for coupling to the stem, said control device having a user-actuated controller for regulating application of negative pressure to the lumen that is for application of suction.

3. The therapeutic device of claim 2, wherein the hand-held control device comprises a housing for coupling to the stem, and a handle, and wherein the user-actuated controller comprises trigger buttons for user actuation positioned on the handle.

4. The therapeutic device of claim 2, wherein the hand-held control device comprises a coupler for connection to a suction source.

5. The therapeutic device of claim 1, wherein the needle is mounted at an acute angle to a longitudinal axis of the stem.

6. The therapeutic device of claim 1, wherein the distal end of the stem further comprises a hub supporting the suction cup and the needle.

7. The therapeutic device of claim 6, wherein the hub includes a conduit to receive a liner defining the lumen that is for application of suction and is surrounded by a flexible sleeve which retains the hub in place.

8. The therapeutic device of claim 7, wherein the suction cup is formed from the flexible sleeve.

9. The therapeutic device of claim 7, wherein the flexible sleeve comprises a silicone over-molded construction.

10. The therapeutic device of claim 1, further comprising a housing having a syringe pusher for mounting a syringe with the therapeutic fluid in fluid communication with the lumen linked with the needle for delivery of the therapeutic fluid.

11. The therapeutic device of claim 1, wherein the stem further comprises a plurality of sensor electrodes at the distal end, and the therapeutic device further comprises a circuit for applying drive signals to the plurality of sensor electrodes and a sensor circuit for monitoring at least one electrical parameter to determine if the plurality of sensor electrodes are in contact with the tympanic membrane or in contact with the ear canal, and to generate an output to indicate at an output device whether the plurality of sensor electrodes are in contact with the tympanic membrane.

12. The therapeutic device of claim 11, wherein at least one sensor electrode in the plurality of sensor electrodes comprises the needle.

13. The therapeutic device of claim 12, wherein at least one sensor electrode in the plurality of sensor electrodes comprises a non-lumen needle spaced apart from the needle.

14. The therapeutic device of claim 11, further comprising a hand-held control device for coupling to the stem and having a user-actuated controller for controlling application of negative pressure to the suction lumen that is for application of suction, and wherein the output device is mounted to the hand-held control device.

15. The therapeutic device of claim 1, wherein there is a gap in a longitudinal direction of the stem between a distal end of the needle and a plane formed by a distal edge of the suction cup before application of the suction.

16. The therapeutic device of claim 15, wherein the plane formed by the distal edge of the suction cup before application of the suction is at an acute angle relative to a longitudinal axis of the stem.

* * * * *